United States Patent [19]

Uhala

[11] Patent Number: 5,423,748
[45] Date of Patent: Jun. 13, 1995

[54] PAIN COMFORTER SYSTEM

[76] Inventor: Dominic Uhala, 532 Madison Ave., Albany, N.Y. 12208

[21] Appl. No.: 106,520

[22] Filed: Aug. 16, 1993

[51] Int. Cl.6 ............................................ A61M 31/00
[52] U.S. Cl. ................................. 604/67; 128/DIG. 13
[58] Field of Search ........................ 604/50, 65, 66, 67; 128/DIG. 13, DIG. 6

[56] References Cited

U.S. PATENT DOCUMENTS

| | | | |
|---|---|---|---|
| 3,192,473 | 6/1965 | Marsh | 128/DIG. 13 |
| 3,618,602 | 11/1971 | Shaw | 604/66 |
| 4,010,749 | 3/1977 | Shaw | 604/66 |
| 4,320,757 | 3/1982 | Whitney et al. | 604/67 |
| 4,647,281 | 3/1987 | Carr | 604/50 |
| 4,684,367 | 8/1987 | Schaffer et al. | 128/DIG. 13 |
| 4,688,577 | 8/1987 | Bro | 604/66 |
| 4,898,578 | 2/1990 | Rubalcaba, Jr. | 128/DIG. 13 |

*Primary Examiner*—C. Fred Rosenbaum
*Assistant Examiner*—Mark Bockelman
*Attorney, Agent, or Firm*—Hugh E. Smith

[57] ABSTRACT

A pain comforter system for providing pain relieving medication to a patient at a rate which is variable as a function of changes in conditions, this system comprising a line for feeding medication from a source to the patient; a pump to feed the medication; means to sense the conditions of the patient and the medication; and a controller coupled to the sensors adapted to energize and de-energize the pump as a result of the sensed conditions.

1 Claim, 3 Drawing Sheets

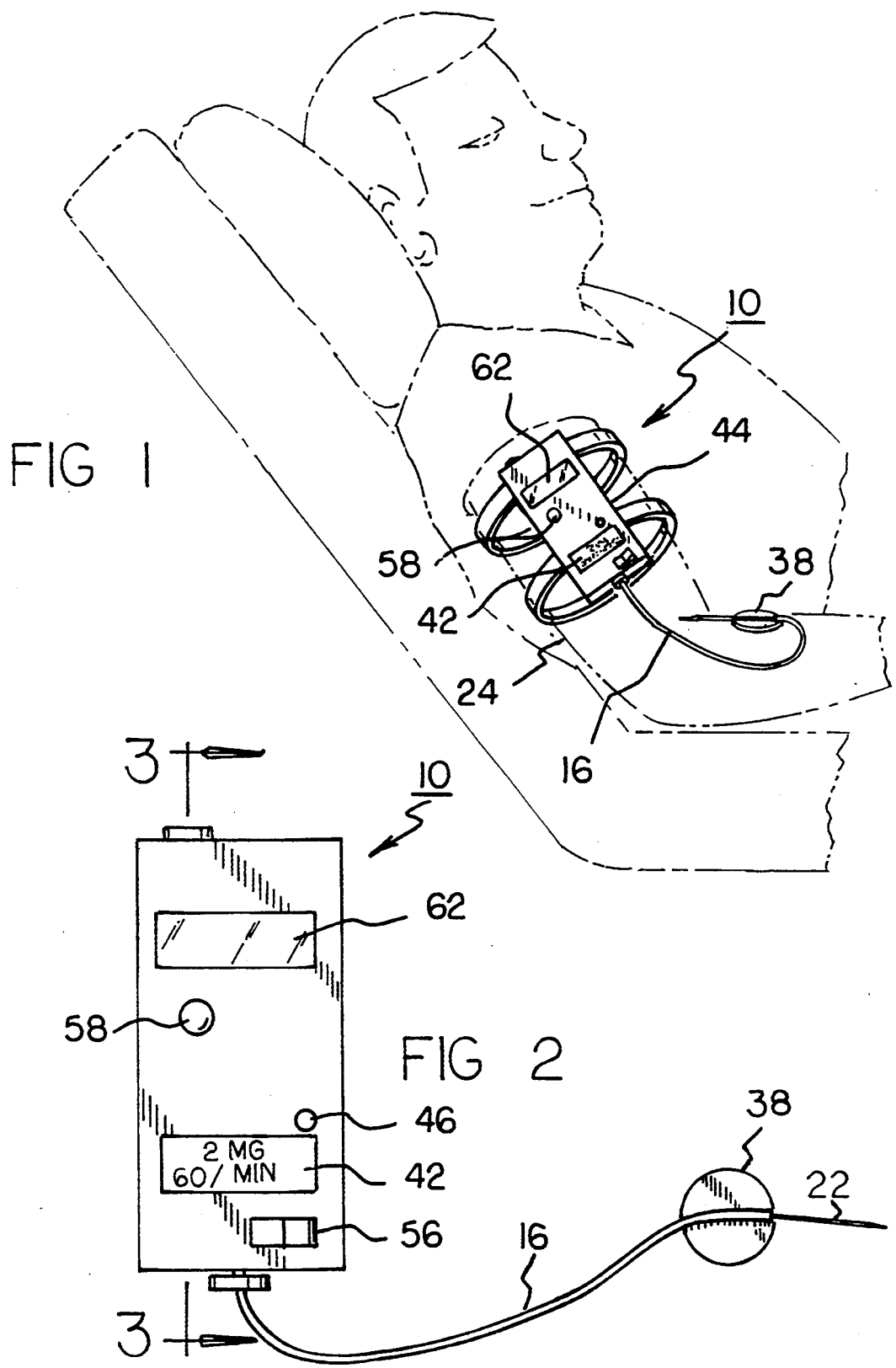

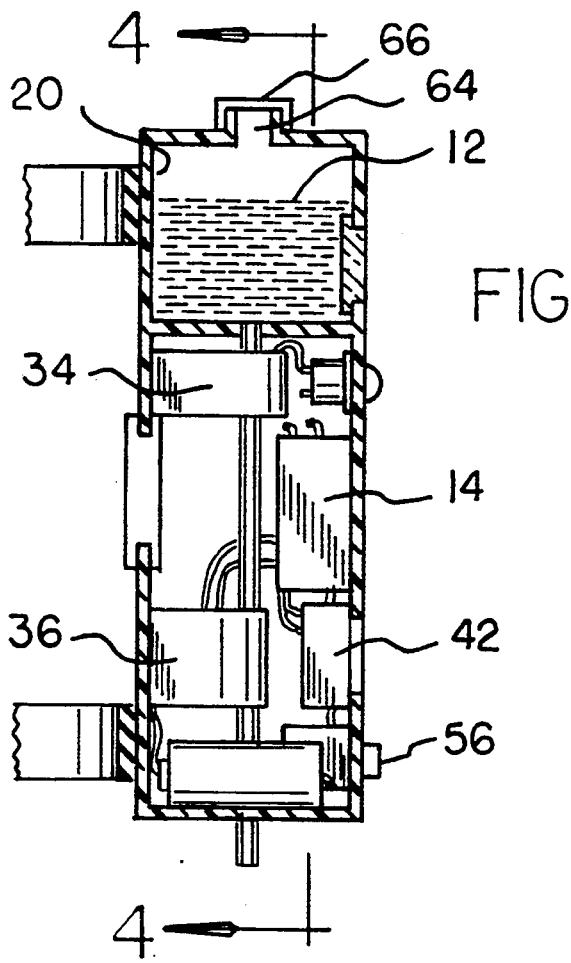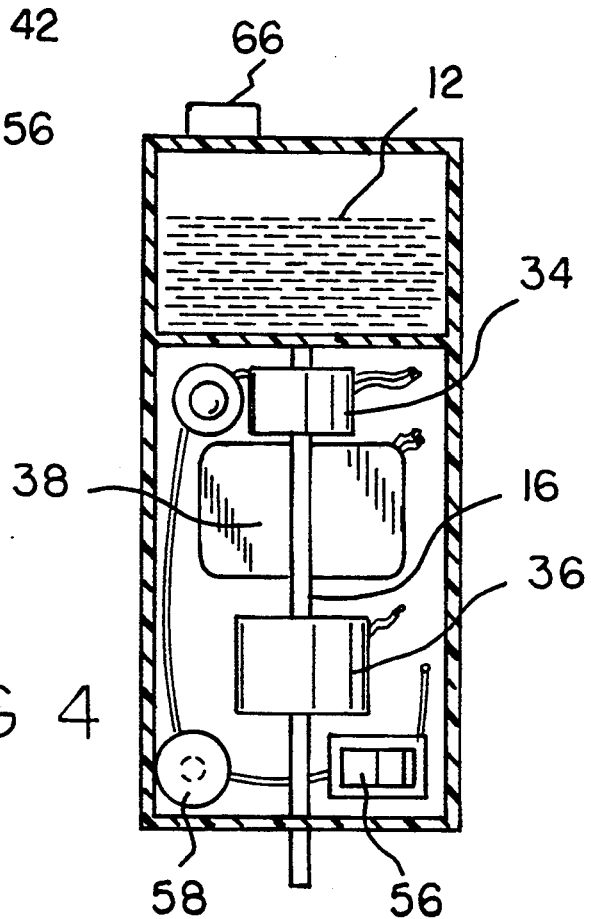

PAIN COMFORTER SYSTEM

BACKGROUND OF THE INVENTION

1. Field of the Invention

The present invention relates to pain comforter system and more particularly to a system with a line for feeding pain relieving medication from a source to a needle inserted in the patient with means to sense the temperature of the patient and the concentration of the medication and to initiate or terminate the feeding of the medication as a function of the sensed condition.

2. Description of the Prior Art

The use of pain comforter systems is known in the prior art. More specifically, pain comforter systems heretofore devised and utilized for the purpose of relieving pain are known to consist basically of familiar, expected and obvious structural configurations, notwithstanding the myriad of designs encompassed by the crowded prior art which have been developed for the fulfillment of countless objectives and requirements.

In this respect, the pain relieving system according to the present invention substantially departs from the conventional concepts and designs of the prior art, and in so doing provides an apparatus primarily developed for the purpose of relieving pain in response to sensed conditions and under the control of the physician and patient.

For example, medication injecting systems utilizing gravity for the establishment of a saline line are disclosed in U.S. Pat. Nos. 4,465,471 to Harris; 4,915,688 to Bischof; and 4,973,328 to Smith. None of these systems are controlled by a computer or modified in response to changing conditions of the medication concentration or patient temperature. U.S. Pat. No. 4,206,757 to Grandadam discloses apparatus for inserting pain relieving medication to a patient but it has no controls whatsoever. U.S. Pat. No. 3,888,253 to Ridgway discloses the providing of medication but such providing of medication is done orally. Lastly, U.S. Pat. No. 4,451,253 to Harman discloses the injecting of solid medication through a device similar to a hypodermic needle but having no controls whatsoever.

Therefore, it can be appreciated that there exists a continuing need for new and improved pain comforter systems. In this regard, the present invention substantially fulfills this need.

SUMMARY OF THE INVENTION

In view of the foregoing disadvantages inherent in the known types of pain comforter systems now present in the prior art, the present invention provides an improved system construction wherein the same can be utilized for relieving pain at a rate controlled by patient temperature and concentration of the medication. As such, the general purpose of the present invention, which will be described subsequently in greater detail, is to provide a new and improved pain comforter apparatus which has all the advantages of the prior art system and none of the disadvantages.

To attain this, the present invention essentially comprises a pain comforter system for providing pain relieving medication to a patient at a rate prescribed by a physician and monitored by a computer center but variable by changes in patient temperature and medication concentration, the system comprising, in combination a line having a supply of medication at one end and a needle insertable into a patient at the other end; a perfusion pump in the line downstream from the supply to feed the medication from the supply to the needle and a flow regulator in the line downstream from the perfusion pump to determine the concentration of the medication; a temperature sensor to determine the temperature of the patient to receive the medication; a computer center coupled to the temperature sensor and flow regulator to monitor the patient temperature and medication concentration, the computer sensor also coupled to the pump to provide an output for activating and inactivating pump as a function of the initial setting of the computer center as well as the input from the temperature sensor and flow regulator; a display coupling the computer center to indicate the sensed conditions of patient temperature and medication concentration; a power circuit coupled to the computer center under the control of the patient to energize and de-energize the system, the power circuit including an on/off switch, a battery and a power indicator lamp; and straps coupling the system to an appendage of the patient with the temperature sensor in contact with the patient's skin and the needle inserted into the patient's skin.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved pain comforter system which has all the advantages of the prior art systems and none of the disadvantages.

It is another object of the present invention to provide a new and improved pain comforter system which may be easily and efficiently manufactured and marketed.

It is a further object of the present invention to provide a new and improved pain comforter system which is of a durable and reliable construction.

An even further object of the present invention is to provide a new and improved pain comforter system which is susceptible of a low cost of manufacture with regard to both materials and labor, and which accordingly is then susceptible of low prices of sale to the consuming public, thereby making such systems economically available to the buying public.

Still yet another object of the present invention is to provide a new and improved pain comforter system which provides in the apparatuses of the prior art some of the advantages thereof, while simultaneously overcoming some of the disadvantages normally associated therewith.

Still another object of the present invention is to provide a new and improved a pain comforter system for providing pain relieving medication to a patient at a rate which is variable as a function of changes in conditions, this system comprising a line for feeding medication from the source to the patient; a pump to feed the medication; means to sense the conditions of the patient and medication; and a controller coupled to the sensors adapted to energize and de-energize the pump as a result of the sensed conditions.

Yet another object of the present invention is to maintain a flow of pain relieving medication as a function of the needs of the patient as determined through sensed conditions of patient temperature and medication concentration.

It is a further object of the present invention to feed pain relieving medication to a patient from a source through a pump and needle and to modify the feed rate as a function of sensed conditions of the patient and medication.

Even still another object of the present invention is to provide an initial dispensing rate for pain relieving medication but to allow modifications as a function of changing conditions including the ability of the patient to turn the system off and on.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the pain comforter system constructed in accordance with the principles of the present invention.

FIG. 2 is a elevational view of the system shown in FIG. 1.

FIG. 3 is a sectional view taken along line 3—3 of FIG. 2.

FIG. 4 is a sectional view taken along line 4—4 of FIG. 3.

DESCRIPTION OF THE PREFERRED EMBODIMENT

Figure 5:
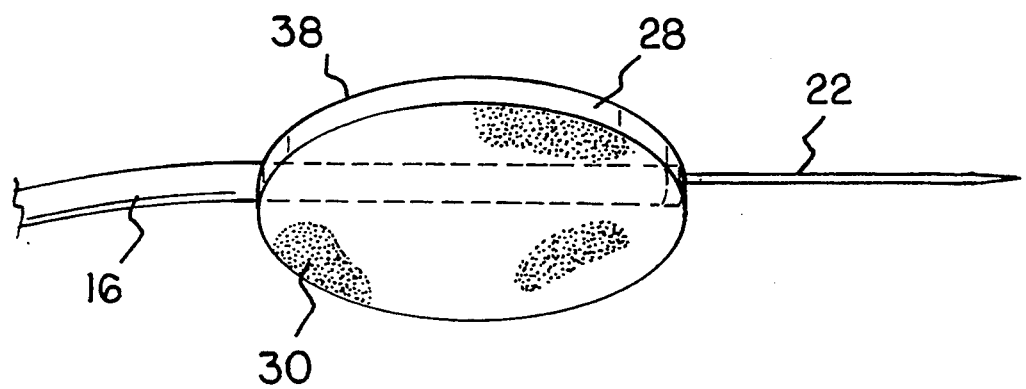
FIG. 5 is a perspective showing of the needle and adhesive backed pad for holding the needle in position.
Figure 6:
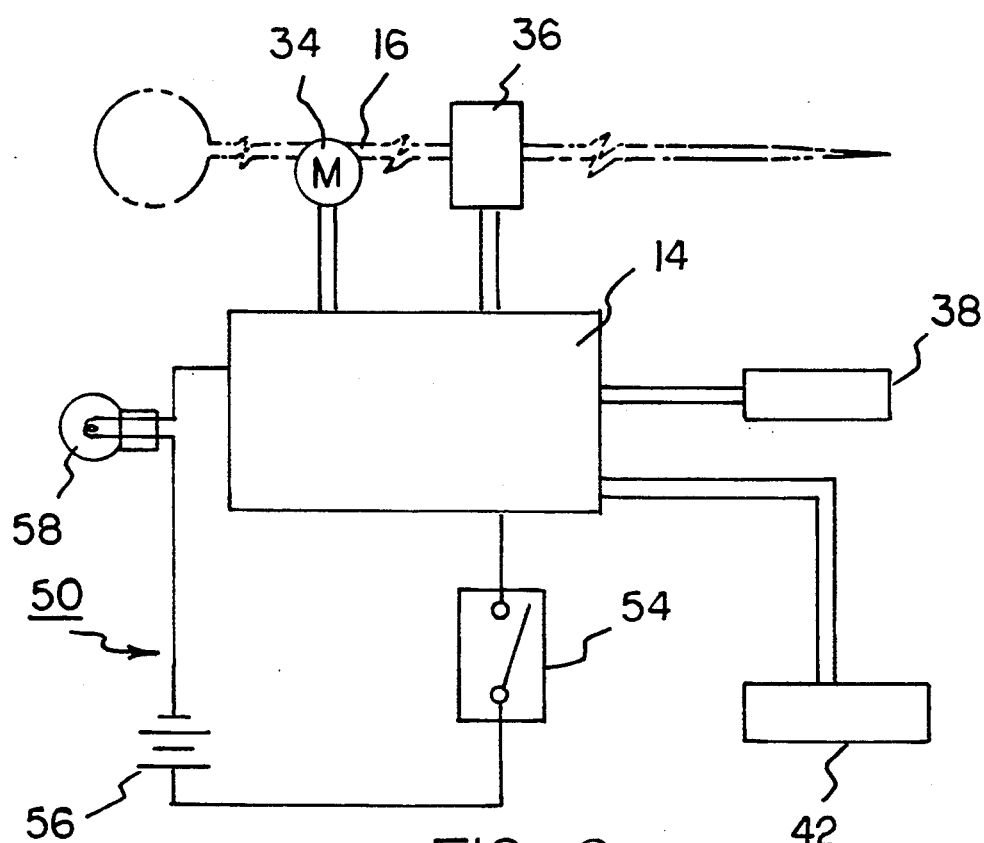
FIG. 6 is a schematic illustration of the components of the system of the prior Figures.

With reference now to the drawings, and in particular to FIG. 1 thereof, a new and improved pain comforter system embodying the principles and concepts of the present invention and generally designated by the reference numeral 10 will be described.

More specifically, it will be noted that pain comforter system 10 of the present invention is for providing pain relieving medication 12 to a patient. The medication, a fluid, is adapted to be dispensed at a rate prescribed by a physician but monitored by a controller or computer center 14 and variable by changes in patient temperature and medication concentration.

The system includes a line 16 through which the medication, to be dispensed for pain relieving purposes, travels from the supply 20 of medication at one end of the line to a needle 22 at the other end of the line. The needle is adapted to be inserted into a vein or muscle of a patient 24 as appropriate for the particular condition of the patient. In association therewith, a pad 28, backed with an adhesive 30 is secured to the line near the needle in order to assure that the needle remains properly inserted for the purpose of providing the pain relieving medication.

Next following the supply is a perfusion pump 34 in the line 16. The perfusion pump functions when energized to feed the medication 12 through the line 16 from the supply 20 to the needle 22. Downstream in the line from the pump is a flow regulator 36. The flow regulator functions to determine the concentration of the medication being fed. The medication concentration and the patient temperature are inputs which may be utilized to vary the energization of the pump and the feeding of the medication.

Another input to the system for varying the flow rate is a temperature sensor 38. The preferred temperature sensor is simply a contact pad 28 in facing contact with the skin of the patient. The temperature sensor 38 determines the temperature of the patient to provide another input for being considered by a controller in determining whether or not the pump should activated or inactivated. Changes in the temperature of the patient might be caused by stress or a wide variety of factors but will, generally, require a change in medication.

The central functioning component of the system is a computer center 14. It is electrically coupled to the temperature sensor 38 and the flow regulator 36 to provide inputs. These inputs to the computer center function to monitor patient temperature and medication concentration. Such inputs are analyzed at the computer center in association with the flow rate by the physician as initially prescribed. With such information being analyzed, the computer center functions to activate or inactivate the pump 34 appropriately in an effort to maintain the proper quantity of medication to the patient in accordance with the patient's needs as well as the physician's diagnosis and indicated treatment.

In association with the functioning components of the system as described above, a display panel 42 functioning as a monitor is provided on the exterior surface of the housing 44. The display panel is coupled with the computer center to provide an indicated readout of the sensed conditions of the patient temperature and the concentration of the medication. The display panel may be illuminated at all times. It is preferred, however, that a button 46 be provided thereadjacent to illuminate the display panel to have a readout of the conditions being monitored.

The last functioning component of the system as described above is a power circuit 50. The power circuit is coupled to the computer center 14 and is under the control of the patient. The power circuit includes a series positioned on/off switch 54, battery 56 and power indicator lamp 58. In this manner, the patient may control the on/off switch to thereby render the entire system operable or inoperable as may be desired by the wishes of the patient. A window 62 in the housing allows for viewing of medication 12 in the source 20 for the patient or physician to add additional medication as may be needed through an aperture 64 covered by a cap 66.

The last element of the system are a pair of straps secured to the housing for coupling the system to an appendage of the patient preferably the arm as shown in FIG. 1. Other appendages include the leg. In the alternative, the system could be used in any part of the patient's body as might be needed under the conditions.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A pain comforter system for providing pain relieving medication to a patient at a rate prescribed by a physician and monitored by a computer center but variable by changes in patient temperature and medication concentration, the system comprising, in combination:

a housing containing a supply of medication and removably positionable on a patient's appendage;

a line coupled to the housing and the supply of medication at one end and a needle insertable into a patient at the other end;

a perfusion pump within the housing in the line downstream from the supply to feed the medication from the supply to the needle and a flow regulator within the housing in the line downstream from the perfusion pump for sensing the concentration of the medication fed by the pump;

a computer center within the housing coupled to the temperature sensor and flow regulator to monitor the patient temperature and medication concentration, the temperature sensor also coupled to the pump to provide an output for activating and inactivating the pump as a function of the initial setting of the computer center as well as the input from the temperature sensor for feeding fluid to the needle through the flow regulator;

a display coupling the computer center to indicate the sensed conditions of patient temperature and medication concentration;

a power circuit coupled to the computer center under the control of the patient to energize and de-energize the system, the power circuit including an on/off switch, a battery and a power indicator lamp; and straps attached to the housing and coupling the entire system to an appendage of the patient with the temperature sensor in contact with the patient's skin and the needle inserted into the patient's skin.

* * * * *